United States Patent [19]

Mayer et al.

[11] 4,142,047
[45] Feb. 27, 1979

[54] SUBSTITUTED TRIAZAADMANTANE COMPOUNDS

[75] Inventors: Norbert Mayer, Gersthofen; Gerhard Pfahler, Augsburg; Hartmut Wiezer, Gersthofen, all of Fed. Rep. of Germany

[73] Assignee: Hoechst Aktiengesellschaft, Frankfurt am Main, Fed. Rep. of Germany

[21] Appl. No.: 786,464

[22] Filed: Apr. 11, 1977

[30] Foreign Application Priority Data

Apr. 15, 1976 [DE] Fed. Rep. of Germany ....... 2616799

[51] Int. Cl.$^2$ ............................................ C07D 251/72
[52] U.S. Cl. ............................. 544/180; 260/45.8 NT; 542/417
[58] Field of Search ........................................ 544/180

[56] References Cited

U.S. PATENT DOCUMENTS

| | | | |
|---|---|---|---|
| 3,575,974 | 4/1971 | Hodge | 544/180 |
| 4,012,384 | 3/1977 | Nielsen | 544/180 |

*Primary Examiner*—John M. Ford
*Attorney, Agent, or Firm*—Connolly and Hutz

[57] ABSTRACT

7-[N-(2-alkylidenimino-isobutylamino)]-1,3,5-triazaadamantanes and 7-[N-(2-arylidenimino-isobutylamino)]-1,3,5-triazaadamantane are prepared from 7-amino-1,3,5-triazaadamantane by two condensation steps. The new compounds are very good stabilizers against decomposition of polymers by heat and UV-light.

3 Claims, No Drawings

SUBSTITUTED TRIAZAADMANTANE COMPOUNDS

The invention is concerned with derivatives of 7-amino-1,3,5-triaza-adamantane, a process for their production and their use for stabilizing organic polymers against the decomposing action of light, especially ultraviolet light, which becomes evident in the discoloration and/or embrittlement of polymers.

The new compounds have the general formula

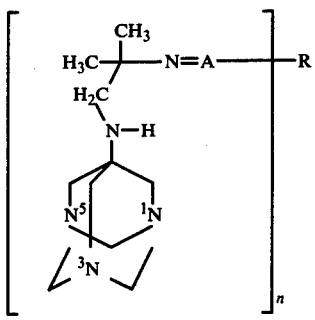 (I)

in which n = 1 or 2, and A represents two hydrogen atoms or the group =CH— and in the latter case, when n = 1, R represents an alkyl radical containing 1 to 17 carbon atoms optionally substituted by a hydroxyl group, or an aryl radical containing 6 to 10 ring carbon atoms optionally substituted by 1 or 2 halogen atoms or an alkyl radical containing 1 to 12 carbon atoms, or an aralkyl radical containing a total of 7 to 10 carbon atoms, and, when n = 2, R represents a corresponding alkylene or arylene radical.

Representative members of the triaza-adamantane compounds of the invention are, for example:

7-[N-(2-Aminoisobutylamino)]-1,3,5-triaza-adamantane.
7-[N-(2-Butylidenimino-isobutylamino)]1,3,5-triaza-adamantane.
7-[N-(2-Isobutylidenimino-isobutylamino)]-1,3,5-triaza-adamantane.
7-[N-(2-Isopentylidenimino-isobutylamino)]-1,3,5-triaza-adamantane
7-[N-(2-Hydroxy-tert.-pentylidenimino-isobutylamino)]-1,3,5-triaza-adamantane.
7-[N-(2-Benzylidenimino-isobutylamino)]-1,3,5-triaza-adamantane.
7-[N-(2-p-Methylbenzylidenimino-isobutylamino)]-1,3,5-triaza-adamantane.
7-[N-(2-p-Isopropylbenzylidenimino-isobutylamino)]-1,3,5-triaza-adamantane.
7-{N-[2-(1-Phenyl)-propylidenimino-isobutylamino]}-1,3,5-triaza-adamantane.
7-[N-(2-p-Chlorobenzylidenimino-isobutylamino)]-1,3,5-triaza-adamantane.
p-Xylylidene-bis-{7-[N-(2-imino-isobutylamino)]-1,3,5-triaza-adamantane}.

The production of the new compounds starts from 7-amino-1,3,5-triaza-adamantane, which may be prepared by known methods [e.g. E. B. Hodge, J. Org. Chem. 37 (1972), 2, pages 320 and 321; A. T. Nielsen, J. Heterocycl. Chem. 12 (1975), pages 161–164]. By the reaction of this compound with 2-methyl-2-nitropropanol-1 there is obtained 7-[N-(2-nitroisobutylamino)]-1,3,5-triaza-adamantane. In a modification of the procedure of E. B. Hodge (loc.cit.), according to which the reactants are heated together in methanol and yields of only about 25% are obtained, the reaction is carried out in accordance with the invention by working at 120° to 190° C., and preferably 160° to 190° C., in an organic solvent which acts simultaneously as an entraining agent for the water of reaction that is formed. An especially useful solvent is 1,3,5-trimethylbenzene (mesitylene). The yield in this stage of the process is then almost quantitative.

The 7-[N-(2-nitroisobutylamino)]-1,3,5-triaza-adamantane is then catalytically hydrogenated, which may be carried out by the usual methods. An especially recommended method of hydrogenation consists in treating the nitro-compound dissolved in a solvent, preferably in ethanol, at 10 to 80, and preferably 30° to 40° C., with hydrazine and Raney nickel as catalyst. The yields of 7-[N-(2-aminoisobutylamino)]-1,3,5-triaza-adamantane melting at 180° to 181° C. are around 70% of theory.

From 7-[N-(2-aminoisobutylamino)]-1,3,5-triaza-adamantane, which has the structure of the general formula in which, in this case, A represents two hydrogen atoms, n = 1 and R is lacking, there can be prepared with aldehydes with the splitting off of water the compounds of the general formula in which A represents the group =CH—. The operation is carried out at 60° to 160° C., and preferably 80° to 120° C., in an organic solvent suitable for the azeotropic removal of the water of reaction, preferably a liquid aromatic hydrocarbon such as benzene or toluene with the addition of 0.01 to 2.0% by weight, calculated on the amino-compound, of an acid catalyst, preferably a strong acid, especially para-toluene sulphonic acid. Ammonium acetate may also be used as catalyst. The amino-compound and aldehyde are used in the equivalent ratio. When the calculated quantity of water has been removed from the system, the solvent is distilled off and the residue, when necessary, is purified by recrystallisation from, for example, toluene, heptane or petroleum ether.

The course of the reaction is represented by the following scheme:

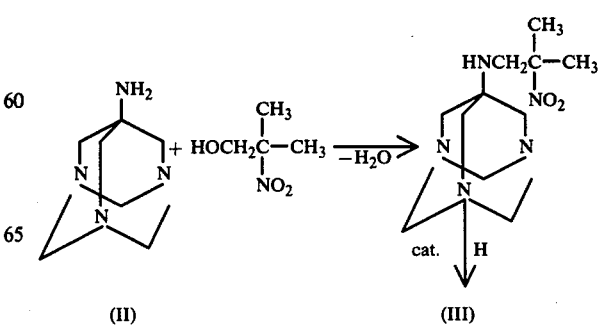

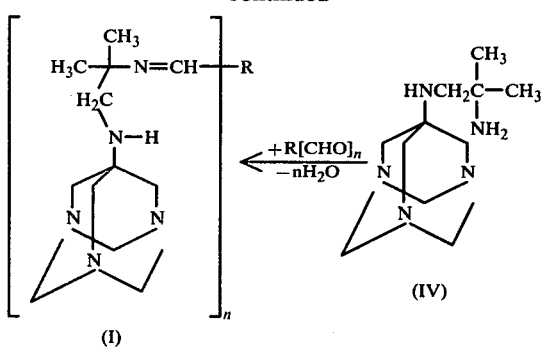

For the reaction with the 7-[N-(2-aminoisobutylamino)]-1,3,5-triaza-adamantane there come into consideration aliphatic mono- and di-aldehydes containing 2 to 18, and preferably 2 to 12, and especially 2 to 5 carbon atoms, which aldehydes may be substituted by a hydroxyl group, and also aromatic mono- and di-aldehydes containing 6 or 10 carbon atoms in the ring. The aromatic aldehydes may be substituted by one or two halogen atoms, preferably chlorine atoms, or by an alkyl radical containing 1 to 12, and preferably 1 to 4, carbon atoms. Finally, aliphatic, aryl-substituted monoaldehydes containing a total of 8 to 12, and preferably 8 to 10, carbon atoms may also be reacted. Suitable monoaldehydes are, for example, n-propylaldehyde, iso-propylaldehyde, butyraldehyde, iso-butyraldehyde, isovaleraldehyde, stearylaldehyde, hydroxy-pivaldehyde, benzaldehyde, 4-methyl-benzaldehyde, 4-isopropyl-benzaldehyde, 4-chlorobenzaldehyde, 2-phenylpropionaldehyde and phenylacetaldehyde. A suitable dialdehyde is, for example, terephthalic dialdehyde. Preferred are the lower aliphatic monoaldehydes and the substituted benzaldehydes. A preferred dialdehyde is terephthalic dialdehyde.

The triaza-adamantane derivatives of the invention impart to organic polymers an extraordinary stability to degradation by heat or ultraviolet radiation. The colour of the polymer masses is not impaired by the presence of the new compounds.

Among organic polymer masses, which are to be protected against the harmful influence of light and heat, there are to be understood polyolefines such, for example, as polyisoprene, polybutadiene, polystyrene and especially polypropylene and polyethylene of low and high densities, and also ethylene-propylene copolymers, ethylene-butene copolymers, ethylene-vinyl acetate copolymers, styrene-butadiene copolymers and acrylonitrile-styrene-butadiene copolymers. The terms "polyvinyl chloride" and "polyvinylidene chloride" are intended to include homopolymers of vinyl chloride and vinylidene chloride, copolymers of vinyl chloride or vinylidene chloride with vinyl acetate or other olefinically unsaturated monomers. Further suitable polymers are polyacetals, polyesters such, for example, as polyethylene terephthalate, polyamides such, for example, as Nylon-6, Nylon-6,6, Nylon-6,10, polyurethanes and epoxy-resins.

The quantity of the new compounds to be added to the synthetic polymers may vary considerably depending on the nature, the properties and the particular uses of the organic polymers to be stabilized. In general there are used 0.01 to 5 parts by weight, preferably 0.05 to 3 parts by weight, and especially 0.1 to 1.5 parts by weight, calculated on 100 parts by weight of the synthetic polymer. There may be used a single compound or a mixture of several compounds.

The incorporation of the compounds of the invention in organic polymers is carried out by the usual methods. Thus, the stabilizer may be mixed in the form of a powder with the polymer or a solution, suspension or emulsion of the stabilizer may be incorporated in a solution, suspension or emulsion of the organic polymer.

The stabilizers are active alone and also in admixture with the usual light- and heat-stabilizers based on phenolic, sulphidic and phosphorus-containing anti-oxidants.

Among the usual stabilizers are to be understood, for example, in particular: 2,6-di-tert.-butyl-para-cresol, 3,5-di-tert.-butyl-4-hydroxyphenyl-propionic acid ester, alkylidene-bis-alkylphenols, thio-dipropionic acid esters of fatty alcohols and also dioctadecyl sulphide and disulphide. As phosphorus-containing compounds there may be mentioned, for example, trisnonyl-phenyl phosphite, distearyl-pentaerythrityl diphosphite, esters of pentaerythritol phosphite, etc. Examples of ultraviolet-absorbers are benztriazole compounds, such as 2-(2'-hydroxy-5'-methylphenyl)-benztriazole, and of quenchers metal chelates.

In the stabilization of the above described chlorine-containing homo- and co-polymerisates, and also chlorinated polyolefins such, for example, as chlorinated polyethylene and polypropylene, an addition of the new stabilizers also brings about an improvement in stability to heat and light in the presence as stabilizers of known metal compounds, epoxistabilizers, phosphites and optionally polyhydric alcohols.

Among the metal compounds known as stabilizers there are to be understood in this connection: Calcium, barium, strontium, zinc, cadmium, magnesium, aluminium and lead soaps of aliphatic carboxylic acids or oxycarboxylic acids containing about 12 to 40 carbon atoms, salts of the aforesaid metals with aromatic carboxylic acids such as benzoates or salicylates and also (alkyl-)phenolates of these metals, and also organo-tin compounds such, for example, as dialkyl tin thioglycollates and carboxylates.

Known epoxistabilizers are, for example, epoxidised higher fatty acids such as epoxidised soya bean oil, tall oil, linseed oil or epoxidised butyl oleate and also epoxides of long-chained α-olefins.

As phosphites there are mentioned trisnonyl phenyl phosphite, trislauryl phosphite and also esters of pentaerythritol phosphite.

Polyhydric alcohols may be, for example, pentaerythritol, trimethylol-propane, sorbitol and mannitol, that is to say, preferred alcohols containing 5 to 6 carbon atoms and 3 to 6 hydroxyl groups.

An effective stabilizer combination for halogen-free poly-α-olefines such, for example, as high, medium and low pressure polymerisates of $C_2$ to $C_4$-α-olefines, especially polyethylene polypropylene or copolymerisates of such α-olefines, consists, calculated on 100 parts by weight of polymer, for example, of 0.01 to 5 parts by weight of one of the compounds to be used in accordance with the invention, 0.05 to 5 parts by weight of a phenolic stabilizer, optionally 0.01 to 5 parts by weight of a sulphur-containing costabilizer, and optionally also 0.01 to 3 parts by weight of a basic or neutral metal soap such, for example, as calcium stearate or zinc stearate, and optionally also 0.1 to 5 parts by weight of a phosphite and optionally 0.01 to 5 parts by weight of a known ultraviolet-stabilizer belonging to the group of alkoxy-hydroxy-benzophenones, hydroxyphenyl-benztriazoles, salicylic acid phenol ester, benzoic acid hydroxyphenol ester, benzylidene malonic acid mononitrile ester, and the so-called quenchers such as nickel chelates or hexamethyl-phosphoric acid triamide.

A stabilizer combination for the stabilization of halogen-containing polymers consists, calculated on 100 parts by weight of polymer, for example, of 0.01 to 10 parts by weight of a known epoxistabilizer, 0.05 to 10 parts by weight of a phosphite, 0.1 to 10 parts by weight of a polyhydric alcohol and 0.1 to 5 parts by weight of one of the compounds to be used in accordance with the invention.

In the following is illustrated by reference to a few Examples the process for the production of the new compounds, and the excellent action thereof as light-stabilizers for synthetic plastics compositions.

EXAMPLE 1

51.3 grams of 7-amino-1,3,5-triaza-adamantane, 39.3 grams of 2-methyl-2-nitropropanol-1 and 150 ml of mesitylene are boiled while stirring under reflux and with the separation of the reaction water, until water is no longer formed. After cooling, the sediment is filtered off with suction, washed with some toluene and dried. The resulting 7-[N-(2-nitro-isobutylamino)]-1,3,5-triaza-adamantane need not be further purified. Yield: 82 grams $\doteq$ 97% of theory. Mp. 196° to 202° C.

202 Grams of this compound are suspended in 1300 grams of ethanol and 160 grams of hydrazine hydrate of 80% strength are added. The mixture is then heated, while stirring, to 30° to 40° C. and about 0.5 gram of Raney nickel in the form of an ethanolic suspension is added. When the evolution of gas has subsided, the same quantity of Raney nickel is added. When, with the further addition of Raney nickel the evolution of gas can no longer be observed, the procedure is repeated with one further portion of 160 grams of hydrazine hydrate. The mixture is then boiled under reflux for about one hour, and, after filtering off the Raney nickel, the ethanol is distilled off completely, finally in vacuo. The water of reaction is then distilled off azeotropically with the addition of 500 ml of toluene, and crystallisation is allowed to take place. The residue is filtered off with suction and dried in vacuo.

Yield: 125 grams $\doteq$ 69% theory of 7-[N-(2-aminoisobutylamino)]-1,3,5-triaza-adamantane. Mp. 180° to 181° C.

Analysis for $C_{11}H_{23}N_5$ (molecular weight 225); Calculated: C 58.6% H 10.2% N 31.1%: Found: C 58.5% H 10.0% N 31.4%: $^{13}$C-NMR (decoupled): 28.2ppm, 40.0 ppm, 49.0 ppm, 51.2 ppm, 62.4 ppm, 73.7 ppm.

EXAMPLE 2

7-[N-(2-Benzylidenimino-isobutylamino)]-1,3,5-triaza-adamantane.

11.2 Grams (0.05 mol) of the amino-compound of Example 1, 5.6 grams (0.05 mol) of benzaldehyde and about 0.1 gram of para-toluene sulphonic acid are boiled with 200 ml of toluene while stirring and with the separation of water, until the calculated quantity of water has been formed (about 2 hours). The toluene is then distilled off in vacuo, and the residue is recrystallised from heptane. White crystals melting at 138° to 140° C. Yield: 10.4 grams of purified product.

Analysis for $C_{18}H_{27}N_5$ (molecular weight 313): Calculated: C 69.0% H 8.6% N 22.4%: Found: C 68.7% H 8.8% N 22.4%:

EXAMPLES 3 to 11

In the manner described in Example 2 there were synthesised in each case from 22.5 grams (0.1 mol) of the amino-compound of Example 1 and a series of aldehydes the following triaza-adamantane compounds, which occurred in the form of white crystals. In the following Table are given the data for the preparation and also the analysis data. All the products, with the exception of that of Example 11, were recrystallised from heptane.

| Example No. | Compound | Quantity of aldehyde (g) | Mp. ° C. | for mol.wt. | Calc.,C Fnd. | Calc.H Fnd. | Calc.N Fnd. |
|---|---|---|---|---|---|---|---|
| 3 | 7-[N-(2-butylidenimino-siobutylamino)]-1,3,5-triaza-adamantane | n-butyr-7.2 | 101–102 | $C_{15}H_{29}N_5$ 279 | 64.5 64.2 | 10.0 10.3 | 25.1 25.1 |
| 4 | 7-[N-(2-Isobutylidenimino-isobutyl-amino)]-1,3,5-triaza-adamantane | isobutyr-7.2 | 133 | $C_{15}H_{29}N_5$ 279 | 64.5 64.1 | 10.0 10.1 | 25.1 24.9 |
| 5 | 7-[N-(2-Isopentylidenimino-isobutyl-amino)]-1,3,5-triaza-adamantane | isovaler-8.6 | 107–109 | $C_{16}H_{31}N_5$ 293 | 65.4 65.2 | 10.6 11.0 | 23.8 23.8 |
| 6 | 7-[N-(2-Hydroxy-tert.-pentylidenimino-isobutylamino)]-1,3,5-triaza-adamantane | hydroxy-pival-10.2 | 136 | $C_{16}H_{31}N_5O$ 309 | 62.1 62.0 | 10.0 10.3 | 22.7 22.7 |
| 7 | 7-[N-(2-p-Methylbenzylidenimino-isobutylamino)]-1,3,5-triaza-adamantane | 4-methyl-benz-12.0 | 138 | $C_{19}H_{29}N_5$ 327 | 69.8 69.5 | 8.9 9.0 | 21.4 21.2 |
| 8 | 7-[N-(2-p-Isopropylbenzylidenimino-isobutylamino)]-1,3,5-triaza-adamantane | 4-isopropylbenz-14.8 | 148 | $C_{21}H_{33}N_5$ 355 | 71.0 70.7 | 9.3 9.5 | 19.7 19.4 |
| 9 | 7-{N-[2-(1-phenyl)-propylidenimino-isobutylamino]-1,3,5-triaza-adamantane | 2-phenyl-propion-13.4 | 101 | $C_{20}H_{31}N_5$ 341 | 70.5 70.1 | 9.1 9.5 | 20.4 20.1 |
| 10 | 7-[N-(2-p-Chlorobenzylidenimino-isobutyl-amino)]}-1,3,5-triaza-adamantane | 4-chloro-benz-19.1 | 120 | $C_{18}H_{26}N_5Cl$ 347.5 | 62.2 61.9 | 7.5 7.6 | 20.2 19.9 |
| 11 | p-Xylylidene-bis-7-[N-(2-imino-isobutyl-amino)]-1,3,5-triaza-adamantane | tere-phthal-13.4 | 263 (dec.) | $C_{30}H_{28}N_{10}$ 548 | 65.6 64.8 | 8.8 8.7 | 25.5 24.8 |

EXAMPLE 12

This Example demonstrates the light-stabilizing action of a few of the compounds of the invention when used in a poly-α-olefine.

100 parts by weight of polypropylene having a melting index $i_5$ of about 6 g/10 min. (determined by ASTM D 1238-62 T) and a density of 0.96 were mixed with 0.10 part by weight of a bis-(4'-hydroxy-3'-tert.-butyl-phenol)-butanoic acid ester, 0.15 part by weight of laurin-thiopropionic acid ester, 0.20 part by weight of calcium stearate and 0.30 part by weight of the stabilizer of the invention to be tested.

and homogenized on a two-roller mill at 200° C. for 5 minutes. The synthetic plastics melt was then pressed at 200° C. to form a plate having a thickness of 1 mm. A test body was stamped out in accordance with DIN 63455 from the cold plate. The test body required as a sample for comparison was made in an analogous manner, but without the stabilizer to be tested.

For determining the stability to light the test samples were subjected to irradiation with alternating light on a light-sensitiveness tester of the firm Original Hanau Quarzlampen GmbH ($^R$ Xenotest-150). The irradiation intensity was modulated by six infra-red windows and one ultraviolet window (DIN 53 387). The exposure time was measured in hours after which the absolute elongation at break had fallen to 10%. The elongation at break was determined on a tensile testing machine of the firm Instron at a drawing speed of 5 cm per minute.

The results are collated in the following Table:

| Stabilizer of the invention according to Example: | Period of resistance (hours) |
| --- | --- |
| 1 | >800 |
| 2 | >800 |
| without | 350 |

| Stabilizer of the invention according to Example: (comparison) | Period of resistance (hours) |
| --- | --- |

What is claimed is:

1. A compound of the formula

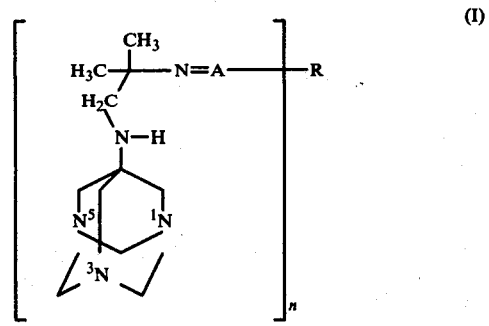

in which
n = 1, and
A represents two hydrogen atoms and R is lacking, or the group =CH— and in the latter case
R represents, when n = 1, an alkyl radical containing 1 to 17 carbon atoms optionally substituted by a hydroxyl group.

2. A compound according to claim 1, in the formula of which n = 1, A represents two hydrogen atoms and R is lacking.

3. A compound according to claim 1, in the formula of which n = 1, A represents the group =CH—, and R represents an n-propyl, isopropyl, isobutyl, or radical.

* * * * *